United States Patent [19]

Liang

[11] Patent Number: 5,905,176

[45] Date of Patent: May 18, 1999

[54] PROCESS FOR THE PRODUCTION OF CYCLOBUTYL HALIDES

[75] Inventor: Shaowo Liang, Kingsport, Tenn.

[73] Assignee: Eastman Chemical Company, Kingsport, Tenn.

[21] Appl. No.: 09/143,223

[22] Filed: Aug. 28, 1998

[51] Int. Cl.$^6$ ............................. C07C 19/00; C07C 19/08
[52] U.S. Cl. ............................................ 570/214; 570/142
[58] Field of Search ...................................... 570/142, 214

[56] References Cited

U.S. PATENT DOCUMENTS 4,158,096   6/1979   Anderson .
5,475,151  12/1995   Liang et al. .
5,502,257   3/1996   Liang et al. .
5,665,718   9/1997   Godel et al. .

FOREIGN PATENT DOCUMENTS 0 380 312 A1   8/1990   European Pat. Off. .

OTHER PUBLICATIONS

Andrea C. Dupont, et al., Synth, Commun., 20(7), 1011–1021 (1990).

*Primary Examiner*—Alan Siegel
*Attorney, Agent, or Firm*—Michael J. Blake; Harry J. Gwinnell

[57] ABSTRACT

Disclosed is a process for the production of cyclobutyl halides such as cyclobutyl chloride and cyclobutyl bromide wherein cyclopropanemethanol is contacted with an aqueous solution of a hydrogen halide at a temperature in the range of greater than 35° C. up to 120° C.

4 Claims, No Drawings

PROCESS FOR THE PRODUCTION OF CYCLOBUTYL HALIDES

The present invention pertains to a process for the production of cyclobutyl halides (CBX) such as cyclobutyl chloride (CBCl) and cyclobutyl bromide (CBBr) from cyclopropanemethanol (CPMO). More specifically, this invention pertains to a process wherein CPMO is contacted with an aqueous hydrogen halide (HX) solution at a temperature of greater than 35° C. up to 120° C. to produce cyclobutyl halides. The cyclobutyl halides thus produced are chemical intermediates useful in the synthesis of other organic compounds such as pharmaceuticals.

Andrea C. Dupont et al., *Synth. Commun.*, 20, 1011–21, (1990) describes the preparation of cyclobutyl chloride by the decarboxylation-chlorination of cyclobutanecarboxylic acid with lead tetraacetate/lithium chloride and the preparation of cyclobutyl bromide is from silver cyclobutanecarboxylate and bromine (Hunsdieker reaction). The complexity of these preparation methods, the requirements of stoichiometric amounts of reagents (lead tetraacetate/lithium chloride or silver nitrate/bromine) and the generation of large amounts of waste make the methods unattractive for commercial-scale production of cyclobutyl halides.

I have discovered that CBX's can be conveniently produced by the treatment of CPMO with aqueous HX solution at a temperature in the range of greater than 35° C. up to 120° C. The process of this invention therefore comprises contacting CPMO with an aqueous HX solution at a temperature in the range of greater than 35° C. up to 120° C. The crude product formed by contacting CPMO with an aqueous HX solution at a temperature in the range of greater than 35° C. up to 120° C. comprises mainly CBX along with small amounts of 4-halo-1-butenes and trace amounts of cyclopropylmethyl halides (CPMX). The crude product forms as an organic phase or layer which may be readily separated, e.g., by decantation, from the aqueous HX solution in which the CPMO is soluble. Cyclobutyl halides are useful intermediates for the production of pharmaceuticals. See, for example, European Published Patent Application EP 0380312 A1. An economical method for the production of cyclobutyl halides provides a means of introducing a highly lipophilic cyclobutane ring on to pharmaceuticals and agrochemicals thereby enhancing their cellular absorption.

The concentration of the hydrogen halide HX in the aqueous HX solution employed in the process may be in the range of about 10 to 80 weight percent, preferably about 20 to 80 weight percent and most preferably 30 to 60 weight percent. The desired concentration of HX aqueous solution can be achieved or maintained by continuously introducing HX gas into the reaction zone of the process. Since CPMO is completely soluble in the aqueous HX solution and the halide products are insoluble in the aqueous phase, the separation of the product (organic phase) is easily achieved by simple decanting. The hydrogen halide HX preferably is hydrogen bromide or, especially, chloride. The process may be carried out at a temperature of greater than 35° C. up to 120° C., preferably from 40 to 80° C., most preferably from 40 to 70° C. At elevated temperature, a CPMX is formed initially and is isomerized to CBX. Thus, the higher temperatures utilized in the present process increase the rate of such isomerization of CPMX to CBX and effectively reduce the concentration of the CPMX in the product to trace quantities. However, the use of excessively high temperature and/or excessively long periods of heating at elevated temperature may cause further isomerization of CBX to 4-halo-1-butene.

The crude product comprising CBX and smaller amounts of the isomeric 4-halo-1-butene and trace amounts of CPMX forms a liquid organic phase which separates from the aqueous HX solution and may be recovered using conventional decantation procedures and equipment. Since CPMO is completely soluble in the aqueous HX solution and the halide products are insoluble in the aqueous phase, the separation of the product (organic phase) may be accomplished by simple decanting. Such differences of solubility between starting material CPMO and product halides in the aqueous HX solution is advantageous for commercial operations since the CPMX formed exists the organic layer while the unreacted CPMO remains in the aqueous layer. Thus, the reaction may be driven to completion while avoiding decomposition and/or isomerization of the CPMX product by prolonged contact with the acid. The 4-halo-1-butenes co-produced in the process of this invention may be isolated by distillation and used as intermediates in the synthesis of pharmaceuticals as described in U.S. Pat. Nos. 4,158,096 and 5,665,718).

The crude product may be purified by distillation. However, heating the CBX product in the presence of an acid can cause significant decomposition of the product. Such catalytic amounts of acid can be generated as a result of the product halide contacting the materials of construction of the equipment, e.g., stainless steels, used for distillation. This acid-catalyzed decomposition/isomerization may be substantially overcome by performing the distillation in the presence of an acid scavenger or acceptor. This may be accomplished by the concurrent addition of an acid scavenger to the column during the distillation. Examples of acid scavengers which may be employed in the distillation include organic amines such as trialkylamines, pyridine and the likes), amides such as N-methylpyrrolidone and N-cyclohexylpyrrolidone, and/or inorganic bases such as sodium or potassium bicarbonate, sodium or potassium carbonates, and carboxylate salts of strong bases e.g., sodium acetate. The preferred acid scavengers are the trialkylamines having boiling points greater than the boiling point of any of the components of the crude product being distilled, e.g., trialkylamines having boiling points of about 100 to 250° C. at ambient pressure. The amount of acid scavenger typically required gives an acid scavenger:crude product weight ratio in the range of about 0.001:1 to 0.1:1.

The products obtained from the process of this invention are mainly CBX, small amounts of 4-halo-1-butene, and only trace amounts (2–3%) of CPMX, which simplifies the separation of CBX by distillation. The boiling point difference of CBX and 4-halo-1-butene is about 7–9° C. The distillation is carried out by feeding the crude CBX to the mid-section of a distillation column operated at a temperature and pressure which provides a column overhead vapor stream comprising 4-halo-1-butene and a column base vapor stream comprising CBX. The distillation preferably is carried out while concurrently feeding an acid scavenger to the upper section of the distillation column. Operation of the distillation in a continuous manner has the advantage of limiting the heating time of the CBX to minimize the possible thermal decomposition. The preferred acid scavengers having a higher boiling point remain in the base of the distillation set.

The other effective way to reduce the isomerization during the distillation is to carry out the distillation under reduced pressure which allows the distillation to be carried out at lower temperature 30–50° C. and to avoid the corrosion problems. The use of equipment such as glass column with packing, which is free of corrosion concerns, for the distillation of crude product can also effectively prevent the isomerization.

The process of this invention may be carried out in a continuous mode of operation. For example, CPMO is introduced continuously into the lower part of the reaction zone wherein CPMO is halogenated by contacting HX aqueous solution. The products formed with lower density than the reaction mixture is separated from the top part of the reaction zone. HX gas is continuously introduced into the lower part of the reaction zone to keep the concentration of the hydrogen halide solution constant. The advantage of the continuous operation is to minimize the contact time of the product CBX with the acid to avoid the further isomerization of CBX to its isomers.

The CPMO used in the present process is readily obtained from the hydrogenation of cyclopropanecarboxaldehyde (CPCA) in the presence of a cobalt or nickel catalyst, for example, by the procedures described in U.S. Pat. No. 5,475,151. CPCA can be produced efficiently and economically by the thermal isomerization of 2,3-dihydrofuran as described in U.S. Pat. No. 5,502,257.

The processes provided by the present invention are further illustrated by the following examples. Gas chromatographic (GC) analyses were performed on a Hewlett-Packard 5890 series II gas chromatography with a 30 meter DB-Wax and a 30 meter DB-17 capillary columns. The identities of the products obtained were confirmed by nuclear magnetic spectrometry and gas chromatography-mass spectrometry by comparison to authentic samples. The percentages specified in the examples are by weight unless otherwise specified.

EXAMPLE 1

To a 300-mL, jacketed flask were placed 36% hydrochloric acid (203 g, 2 mol) and CPMO (36 g, 0.5 mol, 99% purity). The mixture was heated at 55–60° C. for 4.5 hours. After cooling to room temperature, the organic phase was separated by decanting to give 43.2 g of crude product which comprises 78.52% cyclobutyl chloride (CBCl), 18.12% 4-chloro-1-butene and 3.36% cyclopropylmethyl chloride.

Distillation of crude CBCl (prepared by 5 times scale as above) was carried out in a column with stainless steel structure packing with about 50 theoretical plates and a reflux ratio of 30:1. The crude product was fed continuously to the mid-section of the column with tributylamine fed at the top of the column. Pure CBCl was continuously removed as the base vapor after rectification with a short column section packed with Berl saddles. The CBCl having a purity of 96% was obtained with 90% recovery. Most of the by-product CPMCl having a higher boiling point remained in the pot with the amines.

EXAMPLE 2

To a 500-mL jacketed flask were placed 48% hydrobromic acid (340 g, 2 mol) and CPMO (108 g, 1.5 mol, 99% purity). The mixture was heated at 45–50° C. for 4 hours. After cooling to room temperature, the organic phase was separated by decanting to give 168 g of crude product which comprises 59.71% CBBr, 36.63% 4-bromo-1-butene and 3.66% cyclopropylmethyl bromide. Distillation of the crude product with a Teflon spinning band distillation system to give about 90% recovery of CBBr with an purity of 96% and 85% recovery of 4-bromo-1-butene with 98% assay. Small amounts (1% by weight of the total crude product) of N-methylpyrrolidone were added to the base of the distillation system to prevent the decomposition of CBBr during the distillation.

The invention has been described in detail with particular reference to preferred embodiments thereof, but it will be understood that variations and modifications can be effected within the spirit and scope of the invention.

I claim:

1. Process for the production of a cyclobutyl halide which comprises contacting cyclopropanemethanol with an aqueous solution of a hydrogen halide at a temperature or greater than 35° C. up to about 120° C.

2. Process according to claim 1 wherein the hydrogen halide is hydrogen chloride or hydrogen bromide and the concentration of the hydrogen halide in the aqueous solution is about 20 to 80 weight percent.

3. Process according to claim 2 wherein the temperature is in the range of about 40 to 80° C.

4. Process for the production of cyclobutyl chloride which comprises contacting cyclopropanemethanol with a 30 to 60 weight percent hydrogen chloride aqueous solution at a temperature of 40 to 70° C.

* * * * *